United States Patent
Borders et al.

(10) Patent No.: US 7,042,337 B2
(45) Date of Patent: May 9, 2006

(54) COMMUNICATION AND DATA ENTRY DEVICE

(75) Inventors: Richard L. Borders, Cincinnati, OH (US); Richard H. Heimbrock, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 207 days.

(21) Appl. No.: 10/039,342

(22) Filed: Nov. 19, 2001

(65) Prior Publication Data

US 2002/0057203 A1   May 16, 2002

Related U.S. Application Data

(62) Division of application No. 09/187,696, filed on Nov. 6, 1998, now abandoned.
(60) Provisional application No. 60/064,709, filed on Nov. 7, 1997.

(51) Int. Cl.
*G08B 5/00* (2006.01)

(52) U.S. Cl. ............... 340/286.07; 340/539.12; 340/693.5; 340/539.13; 340/539.1; 340/573.1; 340/825.49; 361/679; 361/730; 600/300

(58) Field of Classification Search ............ 340/286.07, 340/573.1, 573.4, 539.1, 539.11, 539.12, 340/539.15, 7.21, 5.84; 704/200, 231, 246, 704/258, 273, 275, 277; 381/110; 455/556.2, 455/556.1, 553.1, 563; 600/301
See application file for complete search history.

(56) References Cited

U.S. PATENT DOCUMENTS

| | | |
|---|---|---|
| 2,976,419 A | 3/1961 | Menke et al. |
| 3,439,320 A | 4/1969 | Ward |
| 3,478,344 A | 11/1969 | Schwitzgebel et al. |

(Continued)

FOREIGN PATENT DOCUMENTS

| | | |
|---|---|---|
| DE | 37 35295 A1 | 4/1988 |
| GB | 2 193 359 | 2/1988 |
| GB | 2 230 365 | 10/1990 |
| GB | 2 265 038 | 9/1993 |
| WO | WO 92/09178 | 5/1992 |
| WO | WO 94/22098 | 9/1994 |
| WO | WO 95/15064 | 6/1995 |
| WO | WO 95/35634 | 12/1995 |
| WO | WO 96/25738 | 8/1996 |
| WO | WO 97/15240 | 5/1997 |
| WO | WO 97/40640 | 10/1997 |

OTHER PUBLICATIONS

Great New Product: Infrared Locator, Teleconnect, Feb., 1986.
T.H. Ooi, "Low Cost RF Identification and Locating System," IEEE Trans. On Consumer Electronics, No. 4, Nov. 1989, pp. 831–839.
United Identifications Systems Corp., Infra–Com, 1989.
The Computer for the 21st Century, Mark Weiser, Scientific American, Sep. 1991.

(Continued)

*Primary Examiner*—Benjamin C. Lee
(74) *Attorney, Agent, or Firm*—Bose McKinney & Evans LLP

(57) ABSTRACT

A personal communication and data entry device comprises a portable housing, an internal controller coupled to the housing, a paging device coupled to the controller, and at least one of a voice recording device, a cellular telephone transceiver, a radio transceiver for two-way communication, and an infrared transmitter coupled to the controller.

31 Claims, 5 Drawing Sheets

U.S. PATENT DOCUMENTS

| | | | |
|---|---|---|---|
| 3,696,384 A | 10/1972 | Lester | |
| 3,714,573 A | 1/1973 | Grossman | |
| 3,739,329 A | 6/1973 | Lester | |
| 3,805,227 A | 4/1974 | Lester | |
| 3,805,265 A | 4/1974 | Lester | |
| 3,988,724 A | 10/1976 | Anderson | |
| 4,151,407 A | 4/1979 | McBride et al. | |
| 4,216,462 A | 8/1980 | McGrath et al. | |
| 4,225,953 A | 9/1980 | Simon et al. | |
| 4,237,344 A | 12/1980 | Moore | |
| 4,275,385 A * | 6/1981 | White | 340/825.49 |
| 4,577,060 A * | 3/1986 | Webb et al. | |
| 4,598,275 A | 7/1986 | Ross et al. | |
| 4,601,064 A | 7/1986 | Shipley | |
| 4,610,254 A * | 9/1986 | Morgan et al. | 607/6 |
| 4,649,385 A | 3/1987 | Aires et al. | |
| 4,706,689 A | 11/1987 | Man | |
| 4,717,261 A * | 1/1988 | Kita et al. | 368/63 |
| 4,728,928 A | 3/1988 | Shipley | |
| 4,740,792 A | 4/1988 | Sagey et al. | |
| 4,814,751 A | 3/1989 | Hawkins et al. | |
| 4,837,568 A | 6/1989 | Snaper | |
| 4,843,640 A | 6/1989 | Juengel | |
| 4,857,716 A * | 8/1989 | Gombrich et al. | 235/375 |
| 4,885,571 A | 12/1989 | Pauley et al. | |
| 4,940,963 A | 7/1990 | Gutman et al. | |
| 4,955,000 A | 9/1990 | Nastrom | |
| 4,967,195 A | 10/1990 | Shipley | |
| 4,968,966 A * | 11/1990 | Jasinski et al. | 340/825.44 |
| 4,979,217 A | 12/1990 | Shipley | |
| 4,981,141 A | 1/1991 | Segalowitz | |
| 4,990,892 A | 2/1991 | Guest et al. | |
| 5,012,113 A | 4/1991 | Valentine et al. | |
| 5,014,040 A | 5/1991 | Weaver et al. | |
| 5,027,314 A | 6/1991 | Linwood et al. | |
| 5,036,852 A | 8/1991 | Leishman | |
| 5,038,800 A | 8/1991 | Oba | |
| 5,051,741 A | 9/1991 | Wesby | |
| 5,051,924 A | 9/1991 | Bergeron et al. | |
| 5,062,151 A | 10/1991 | Shipley | |
| 5,119,104 A | 6/1992 | Heller | |
| 5,153,584 A | 10/1992 | Engira | |
| 5,214,421 A | 5/1993 | Vernon et al. | |
| 5,218,344 A | 6/1993 | Ricketts | |
| 5,226,090 A * | 7/1993 | Kimura | 381/110 |
| 5,227,776 A | 7/1993 | Starefoss | |
| 5,231,991 A | 8/1993 | Nelson | |
| 5,245,314 A | 9/1993 | Kah, Jr. | |
| 5,266,944 A | 11/1993 | Carroll et al. | |
| 5,291,399 A | 3/1994 | Chaco | |
| 5,317,309 A | 5/1994 | Vercellotti et al. | |
| 5,319,191 A | 6/1994 | Crimmins | |
| 5,319,355 A * | 6/1994 | Russek | 340/573.1 |
| 5,319,363 A | 6/1994 | Welch et al. | |
| 5,341,412 A | 8/1994 | Ramot et al. | |
| 5,348,008 A * | 9/1994 | Bornn et al. | 600/301 |
| 5,351,149 A | 9/1994 | Crimmins | |
| 5,363,425 A | 11/1994 | Mufti et al. | |
| 5,374,921 A | 12/1994 | Martin et al. | |
| 5,387,993 A | 2/1995 | Heller et al. | |
| 5,390,238 A | 2/1995 | Kirk et al. | |
| 5,396,224 A | 3/1995 | Dukes et al. | |
| 5,402,469 A | 3/1995 | Hopper et al. | |
| 5,412,715 A | 5/1995 | Volpe | |
| 5,417,222 A | 5/1995 | Dempsey et al. | |
| 5,421,177 A | 6/1995 | Sieber et al. | |
| 5,426,425 A | 6/1995 | Conrad et al. | |
| 5,455,851 A | 10/1995 | Chaco et al. | |
| 5,458,123 A | 10/1995 | Unger | |
| 5,461,665 A | 10/1995 | Shur et al. | |
| 5,465,082 A | 11/1995 | Chaco | |
| 5,471,404 A | 11/1995 | Mazer | |
| 5,473,667 A * | 12/1995 | Neustein | 379/57 |
| 5,493,283 A | 2/1996 | Hopper et al. | |
| 5,504,477 A | 4/1996 | Whitright et al. | |
| 5,515,426 A | 5/1996 | Yacenda et al. | |
| 5,525,967 A | 6/1996 | Azizi et al. | |
| 5,534,851 A * | 7/1996 | Russek | 340/573.1 |
| 5,534,876 A | 7/1996 | Erickson et al. | |
| 5,537,459 A | 7/1996 | Price et al. | |
| 5,541,585 A | 7/1996 | Duhame et al. | |
| 5,548,637 A | 8/1996 | Heller et al. | |
| 5,561,412 A | 10/1996 | Novak et al. | |
| 5,572,195 A | 11/1996 | Heller et al. | |
| 5,572,653 A | 11/1996 | DeTemple et al. | |
| 5,576,952 A * | 11/1996 | Stutman et al. | |
| 5,588,009 A | 12/1996 | Will | |
| 5,589,821 A | 12/1996 | Sallen et al. | |
| 5,590,648 A | 1/1997 | Mitchell et al. | |
| 5,594,786 A | 1/1997 | Chaco et al. | |
| 5,600,108 A | 2/1997 | Newham | |
| 5,621,384 A | 4/1997 | Crimmins et al. | |
| 5,627,524 A | 5/1997 | Fredrickson et al. | |
| 5,629,678 A | 5/1997 | Gargano et al. | |
| 5,633,742 A | 5/1997 | Shipley | |
| 5,635,907 A | 6/1997 | Bernard et al. | |
| 5,640,002 A | 6/1997 | Ruppert et al. | |
| 5,640,157 A | 6/1997 | Langeraar | |
| 5,652,570 A * | 7/1997 | Lepkofker | 340/573.4 |
| 5,682,139 A | 10/1997 | Pradeep et al. | |
| 5,682,142 A | 10/1997 | Loosmore et al. | |
| 5,683,423 A * | 11/1997 | Post | 607/5 |
| 5,686,888 A | 11/1997 | Welles, II et al. | |
| 5,689,229 A | 11/1997 | Chaco et al. | |
| 5,697,060 A * | 12/1997 | Akahane | 340/7.31 |
| 5,699,038 A | 12/1997 | Ulrich et al. | |
| 5,714,932 A | 2/1998 | Castellon et al. | |
| 5,722,599 A | 3/1998 | Fries | |
| 5,729,196 A | 3/1998 | Aljadeff et al. | |
| 5,731,757 A | 3/1998 | Layson, Jr. | |
| 5,732,711 A | 3/1998 | Fitzpatrick et al. | |
| 5,737,688 A * | 4/1998 | Sakai et al. | 455/31.2 |
| 5,742,233 A | 4/1998 | Hoffman et al. | |
| 5,745,037 A | 4/1998 | Guthrie et al. | |
| 5,745,272 A | 4/1998 | Shipley | |
| 5,748,084 A | 5/1998 | Isikoff | |
| 5,748,148 A | 5/1998 | Heiser et al. | |
| 5,749,908 A * | 5/1998 | Snell | 607/30 |
| 5,751,246 A | 5/1998 | Hertel | |
| 5,754,125 A | 5/1998 | Pearce | |
| 5,760,687 A | 6/1998 | Cousy | |
| 5,767,788 A | 6/1998 | Ness | |
| 5,771,003 A | 6/1998 | Seymour | |
| 5,793,861 A | 8/1998 | Haigh | |
| 5,815,566 A | 9/1998 | Ramot et al. | |
| 5,818,617 A | 10/1998 | Shipley | |
| 5,822,230 A * | 10/1998 | Kikinis et al. | 708/109 |
| 5,822,418 A | 10/1998 | Yacenda et al. | |
| 5,822,544 A | 10/1998 | Chaco et al. | |
| 5,825,283 A | 10/1998 | Camhi | |
| 5,828,306 A | 10/1998 | Curran | |
| 5,831,533 A | 11/1998 | Kanno | |
| 5,835,907 A | 11/1998 | Newman | |
| 5,838,223 A | 11/1998 | Gallant et al. | |
| 5,838,472 A | 11/1998 | Welch et al. | |
| H1782 H * | 2/1999 | Wicks et al. | 340/825.44 |
| 5,867,821 A * | 2/1999 | Ballantyne et al. | 705/2 |
| 5,872,505 A * | 2/1999 | Wicks et al. | 340/7.3 |
| 5,877,675 A * | 3/1999 | Rebstock et al. | 340/286.07 |
| 5,902,234 A * | 5/1999 | Webb | 600/300 |
| 5,920,287 A | 7/1999 | Belcher et al. | |

| | | | |
|---|---|---|---|
| 5,921,938 A * | 7/1999 | Aoyama et al. ............ 600/509 |
| 5,959,529 A | 9/1999 | Kail, IV |
| 5,970,387 A * | 10/1999 | Yuan ......................... 455/31.2 |
| 5,970,457 A * | 10/1999 | Brant et al. ................. 704/275 |
| 5,973,613 A * | 10/1999 | Reis et al. ............. 340/825.44 |
| 6,009,333 A | 12/1999 | Chaco |
| 6,021,310 A * | 2/2000 | Thorne ...................... 340/7.54 |
| 6,037,879 A | 3/2000 | Tuttle |
| 6,040,773 A | 3/2000 | Vega et al. |
| 6,057,758 A * | 5/2000 | Dempsey et al. ...... 340/539.12 |
| 6,057,782 A * | 5/2000 | Koenig .................. 340/825.44 |
| 6,082,776 A * | 7/2000 | Feinberg ..................... 283/72 |
| 6,085,069 A * | 7/2000 | Sharpe ...................... 455/31.3 |
| 6,091,332 A | 7/2000 | Eberhardt et al. |
| 6,097,301 A | 8/2000 | Tuttle |
| 6,100,804 A | 8/2000 | Brady et al. |
| 6,101,390 A | 8/2000 | Jayaraman et al. |
| 6,104,311 A | 8/2000 | Lastinger |
| 6,114,962 A | 9/2000 | Wiklof et al. |
| 6,118,379 A | 9/2000 | Kodukula et al. |
| 6,121,878 A | 9/2000 | Brady et al. |
| 6,127,928 A | 10/2000 | Issacman et al. |
| 6,130,612 A | 10/2000 | Castellano et al. |
| 6,131,067 A | 10/2000 | Girerd et al. |
| 6,133,832 A | 10/2000 | Winder et al. |
| 6,137,411 A | 10/2000 | Tyren |
| 6,137,412 A | 10/2000 | Herzer |
| 6,141,531 A * | 10/2000 | Willaims et al. ............ 455/555 |
| 6,144,301 A | 11/2000 | Frieden |
| 6,147,592 A | 11/2000 | Ulrich et al. |
| 6,150,921 A | 11/2000 | Werb et al. |
| 6,154,139 A | 11/2000 | Heller |
| 6,177,861 B1 | 1/2001 | MacLellan et al. |
| 6,204,764 B1 | 3/2001 | Maloney |
| 6,204,765 B1 | 3/2001 | Brady et al. |
| 6,204,813 B1 | 3/2001 | Wadell et al. |
| 6,211,781 B1 | 4/2001 | McDonald |
| 6,216,104 B1 * | 4/2001 | Moshfeghi et al. ......... 704/260 |
| 6,252,512 B1 | 6/2001 | Riley |
| 6,259,355 B1 | 7/2001 | Chaco et al. |
| 6,344,794 B1 | 2/2002 | Ulrich et al. |
| 6,353,413 B1 * | 3/2002 | White et al. ................. 342/453 |
| 6,408,272 B1 * | 6/2002 | White et al. ............. 704/270.1 |
| 6,453,281 B1 * | 9/2002 | Walters et al. .............. 704/200 |
| 6,466,801 B1 * | 10/2002 | Leyendecker ............ 455/550.1 |

OTHER PUBLICATIONS

Keeping Track of Alzheimer and Dementia Prone Patients Just Got Easier, Security Tag Systems, Inc., 1991.

The Clock with Sekurmed, 1991.

Infant Monitoring System, Sekurmed.

IBM Technical Disclosure Bulletin, "Portable, Speech-Activated, Electronic Mail System", Jul. 1995, vol. 38 No. 07.

Swatch telecom, "Swatch Talk", Feb. 11, 1999, http://www.swatch.com/telecom/index.php3.

The Financial Post, "Watch Dick Tracy take the time to talk", Jul. 4, 1998, pp. 7–8.

* cited by examiner

COMMUNICATION AND DATA ENTRY DEVICE

BACKGROUND AND SUMMARY OF THE INVENTION

This application is a divisional of U.S. patent application Ser. No. 09/187,696, filed Nov. 6, 1998, now is abandoned, which claims the benefit of U.S. application Ser. No. 60/064,709, filed Nov. 7, 1997, the disclosures of which are expressly incorporated by reference herein.

The present invention relates generally to communication and data entry devices, and particularly to devices for use by personnel such as doctors and nurses in a hospital environment. More particularly, the present invention relates to communication devices carried by medical caregivers for receiving signals directed to members of a hospital team and data entry devices for processing voice information dictated by a caregiver.

Communication devices such as pagers and data entry devices such as dictating machines are known. Caregivers in hospital environments use such devices routinely to receive messages and to record information about patients. For example, doctors and registered nurses may dictate patient status reports or data observed during surgical procedures. In addition, when a team of doctors and nurses are needed in an operating room, separate paging signals are sometimes sent to the pagers of each team member to assemble the team. Hospitals may charge patients on an hourly basis for some medical services and for use of hospital resources such as operating rooms. Therefore, decreasing the time spent assembling teams, decreasing the time spent by team members performing tasks such as dictating patient reports, and decreasing the number of personnel needed on a team each result in decreased medical costs. Furthermore, rapid assembly of a team can be of critical importance when a patient has a life threatening injury or medical condition that requires prompt medical attention.

According to aspects of the present invention, a system for paging members of a medical team includes a paging signal dispatch system and a plurality of pagers. The paging signal dispatch system includes a transmitter configured to broadcast a paging signal configured to page a plurality of pagers simultaneously and a receiver configured to receive a page acknowledge return signal from each of the plurality of pagers. Each pager includes a receiver configured to receive the paging signal, a transmitter configured to send a page acknowledge return signal, and a user input device coupled to the transmitter. The pager is configured to send the page acknowledge return signal based on an input to the user input device.

In illustrative embodiments, the dispatch system transmitter is configured to send a paging signal for direct reception by pager receivers that are within a predetermined distance of the dispatch system. The dispatch system transmitter can be configured to send a paging signal for indirect reception through at least one paging signal repeater by pager receivers that are outside a predetermined distance of the dispatch system. The pager transmitter can be configured to send a page acknowledge return signal for direct reception by the dispatch system receiver. The pager transmitter can be configured to send a page acknowledge return signal for indirect reception through at least one signal repeater by the dispatch system receiver. The dispatch system can be configured to indicate whether each of the plurality has acknowledged a paging signal within a predefined amount of time after sending the paging signal.

In illustrative embodiments, the dispatch system transmitter is configured to broadcast a first paging signal configured to page a first plurality of pagers simultaneously and second paging signal configured to page a second plurality of pagers simultaneously and a receiver configured to receive a page acknowledge return signal from each of the first and second pluralities of pagers. The plurality of pagers includes first and second pluralities of pagers. Each pager includes a receiver configured to receive one of the first and second paging signals, a transmitter configured to send a page acknowledge return signal, and a user input device coupled to the transmitter. Each pager is configured to send the page acknowledge return signal based on an input to the user input device. The dispatch system transmitter is configured to broadcast the first paging signal at a first frequency and the second paging signal at a second frequency different from the first frequency.

In illustrative embodiments, each pager includes a radio transceiver for two-way communication with other pagers. A first plurality of pagers can be configured to communicate at a first frequency and a second plurality of pagers configured to communicate at a second frequency different from the first frequency.

In illustrative embodiments, each pager includes an infrared transmitter configured to send an identifying signal. The dispatch system includes a plurality of infrared receivers configured to receive the identifying signals and is configured to determine locations of pagers based on reception of the identifying signals. The dispatch system is configured to identify a location of a pager that has not acknowledged a paging signal within a predefined amount of time after sending the paging signal. The dispatch system can further be configured to identify a location of a substitute pager if a pager has not acknowledged a paging signal within a predefined amount of time after sending the paging signal, and to send a paging signal to the substitute pager.

In illustrative embodiments, the pager includes a voice recording device. The voice recording device can be voice activated. The recording device can store data in an digital format, and the pager can be configured to transmit the data to a remote system, for example over a wireless communication link.

In illustrative embodiments, the pager includes a display and is configured to store information related to a patient for output on the display. The pager can include a user input device to enter patient information and be configured to transmit entered information to a remote system. The pager can further be configured to receive patient information from a remote system for output on the display.

In illustrative embodiments, the pager includes a cellular telephone transceiver. The pager can be configured to couple to a caregiver's wrist, or to a belt around a caregiver's waist, or to a strap around a caregiver's neck. A flexible sterile sheath can be configured to surround the pager.

According to other aspects of the invention, an integrated personal communication and data entry device includes a portable housing and an internal controller. A paging device and a voice recording device are both coupled to the controller. Either the paging device or the voice recording device can provide the controller. The integrated device can further include a cellular telephone transceiver and/or a radio transceiver for two-way communication coupled to the controller. The voice recording device can be configured to digitize voice data and to transform the digitized voice data into computer readable text data.

According to illustrative embodiments, the integrated device further includes a clock coupled to the controller and the voice recording device is configured to record a time and date from the clock corresponding to recorded voice data. The integrated device can include an input device to enter a user identification code and the voice recording device can be configured to record voice data only after entry of a predefined user identification code. The voice recording device can be configured to record voice data only if the voice data corresponds to predefined voice print information. The voice recording device can be coupled to a transceiver configured to transmit voice information over a wireless communication link to a hospital data system. The voice recording device can be configured to transmit patient identification information to the hospital data system to enable storage of voice information from the voice recording device related to a patient on the hospital data system.

According to illustrative embodiments, the integrated device includes an input device coupled to the housing, an output device coupled to the housing, and a transceiver coupled to the housing to send and receive information over a wireless communication link to a hospital data system. The integrated device is configured to accept patient identification information from the input device, to send the patient identification information to the hospital data system, to receive patient data from the hospital data system based on the patient identification information, and to display the patient data on the output device. The voice recording device can provide the input device. The output device can be a backlit liquid crystal display. The integrated device can be configured to provide at least one prompt on the output device for entry of patient status information based on patient data received from the hospital system. The integrated device can be configured to provide at least one prompt on the output device to record at least one predetermined category of patient status information.

According to still other aspects of the invention, an integrated personal communication and data entry device includes a portable housing, an internal controller, and a paging device and a cellular telephone transceiver coupled to the controller. The integrated device can further include a radio transceiver for two-way communication, an infrared transmitter, and/or a voice recording device According to yet still other aspects of the invention, an integrated personal communication and data entry device includes a portable housing, an internal controller, and a paging device and a radio transceiver for two-way communication coupled to the controller. The integrated device can further include a cellular telephone transceiver, an infrared transmitter, and/or a voice recording device.

According to other aspects of the invention, an integrated personal communication and data entry device includes a portable housing, an internal controller, an a paging device and an infrared transmitter coupled to the controller. The integrated device can further include a cellular telephone transceiver, a radio transceiver for two-way communication, and/or a voice recording device.

According to still other aspects of the invention, a voice operated controller for medical equipment includes a voice recorder configured to digitize and recognize voice commands and a transmitter configured to send commands recognized by the voice recorder to a medical equipment controller. The controller can be configured to send commands over a wireless communication link. The controller can include a housing coupled to the voice recorder and transmitter that is configured to be coupled to a caregiver's head to position an input device for the voice recorder near the caregiver's mouth.

Additional features of the invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which.

DETAILED DESCRIPTION OF DRAWINGS

Figure 1:
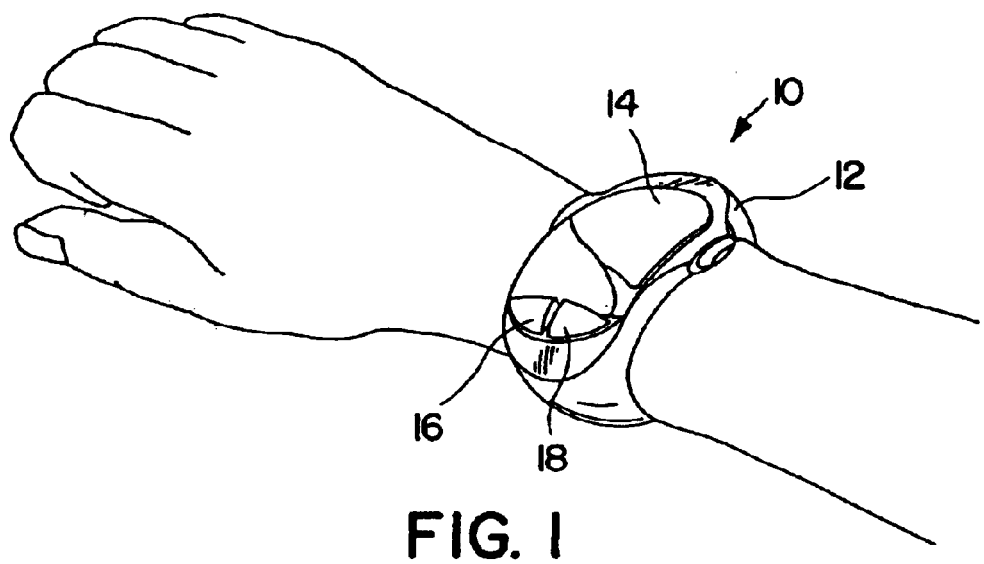
FIG. 1 is a perspective view of a data entry and communication device according to the present invention in a wrist band configuration.

An integrated personal communication and data entry device 10 includes a housing 12 configured to be coupled to a caregiver's wrist, a display 14, and a pair of buttons 16, 18 as shown in FIG. 1. As discussed in more detail below, in various embodiments, integrated device 10 includes some or all of the following within compact housing 12: a paging device, a voice recording device, a cellular telephone device, and a radio communication device. By merging several functions into a single integrated device 10, the present invention increases the efficiency of medical caregivers and reduces costs associated with providing medical services.

Advances in miniaturization of electronic components allows integrated communication and data entry device 10 to contain in a compact package the electronic components needed to perform multiple functions. For example, a single integrated circuit can digitize and store voice data for subsequent access or processing. Infrared transmitters allow for real-time monitoring of the location of device 10 throughout a building equipped with infrared receivers. Commercially available radio transceivers provide two-way "walkie talkie" communication functions in a very small, power efficient package. Pager technology likewise provides for diminutive packaging, and is readily adapted to signal multiple members of a medical team simultaneously. Integrating these various technologies, each of which by itself is known to those skilled in the art, will benefit medical service providers and patients alike by increasing the efficiency of providing medical services.

Figure 2:
FIG. 2 is a perspective view of an the device of FIG. 1 coupled to a caregiver's belt.
Figure 3:
FIG. 3 is a perspective view of a caregiver wearing the device of FIG. 1, showing reception of voice data for use either as a data recorder or as a two-way communication device.
Figure 4:
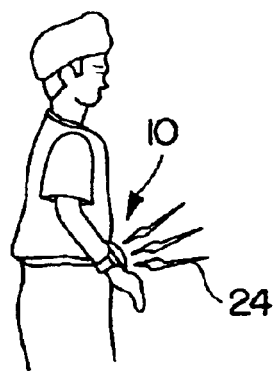
FIG. 4 is a perspective view somewhat similar to FIG. 3 showing automatic reception of signal information.

Integrated device 10 provides a convenient, highly portable apparatus for use by medical caregivers as shown in FIGS. 2–4. For situations where it is inconvenient or undesirable to couple device 10 to a caregiver's wrist, device 10 can readily be affixed to a caregiver's belt 20 as shown in FIG. 2, attached to a strap or necklace (not shown) worn around a caregiver's neck, or carried about by a caregiver in any manner that is convenient. Integrated device 10 provides both a recording and a two-way communication function that is constantly accessible for hands-free use by the caregiver as shown in FIG. 3, allowing for input of voice signals 22 for dictation of information such as notes, instructions, etc., as well as for communication with other personnel who are not in the caregiver's immediate vicinity. Including built-in paging and radio communication devices in integrated device 10 provides for constant reception of incoming communication signals 24 to maintain the caregiver's accessibility, both within a hospital environment as well as from remote locations.

Figure 9:
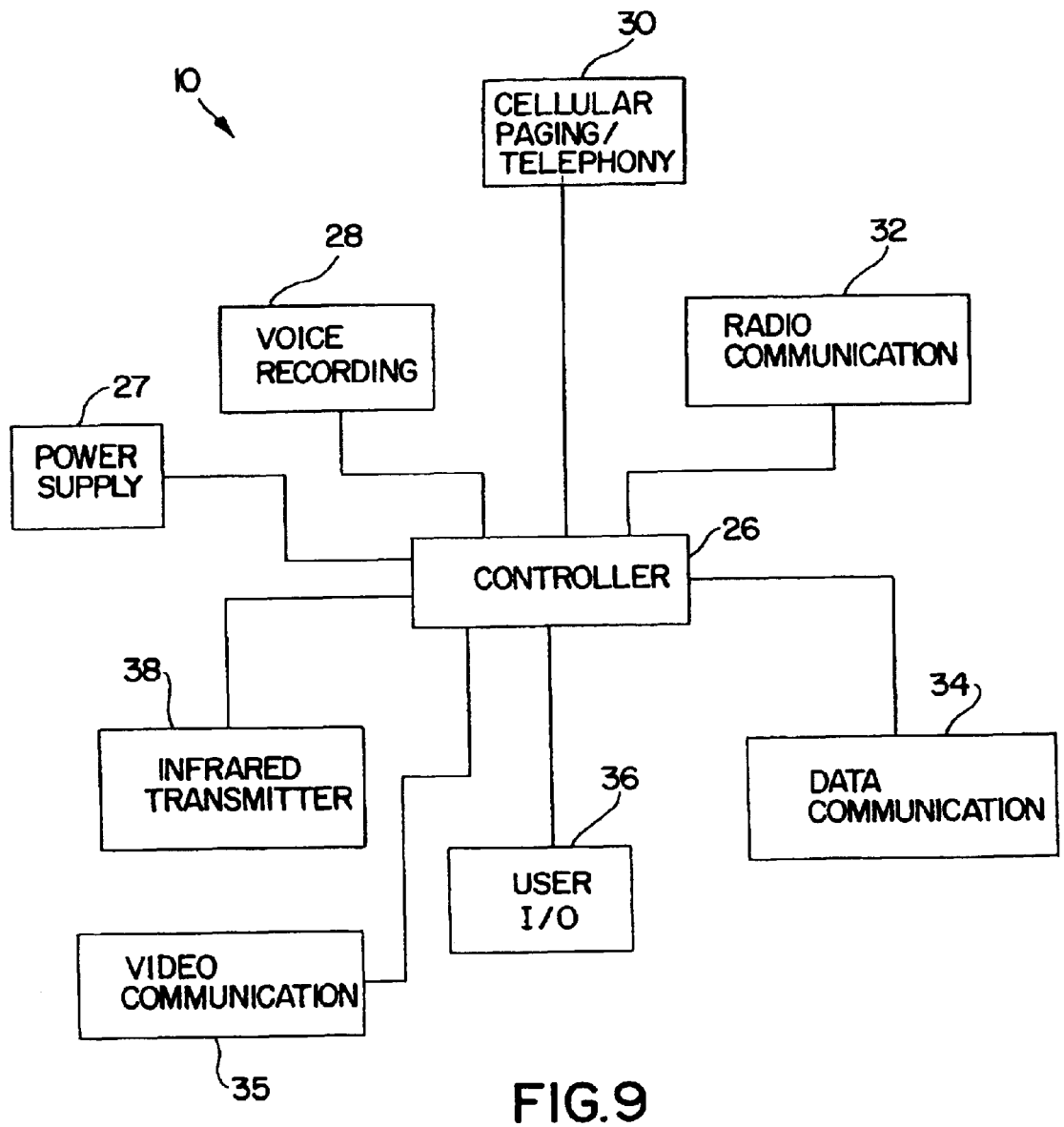
FIG. 9 is a block diagram of an architecture of an integrated data entry and communication device according to the present invention.

An illustrative architecture for integrated device 10 includes a controller 26 coupled to several interface modules as shown in FIG. 9. Controller 26 can be a microprocessor or microcontroller, with either on-board or separate memory, or it can be any type of specialized or off-the-shelf component, such as a high speed digital signal processor, that includes or provides for integrating the various functions as required for device 10. Those skilled in the art understand that there are many known techniques for providing or integrating the various functions as discussed below.

Controller 26 is coupled to a voice recording module 28, a cellular paging and telephony module 30, a radio communication module 32, a wireless data communication module 34, a user input/output module 36, and an infrared transmitter module 38. A power supply 27, such as a battery, is included in device 10 and coupled to one or more of controller 26 and modules 30, 32, 34, 36, 38 as shown, for example, in FIG. 9. Those skilled in electronics understand that any number or portions of these modules can be provided by a single module or by controller 26, and that these modules can be cross-coupled as needed. For example, common circuitry for processing voice data is most conveniently provided by a microphone input included in user input/output module 36 and shared directly with voice recording, cellular paging and telephony, and radio communication modules 28, 30, 32. Similarly, radio and data communication modules 32, 34 can be provided by a single module, voice recording can be handled by software provided in controller 26, etc.

Figure 10:
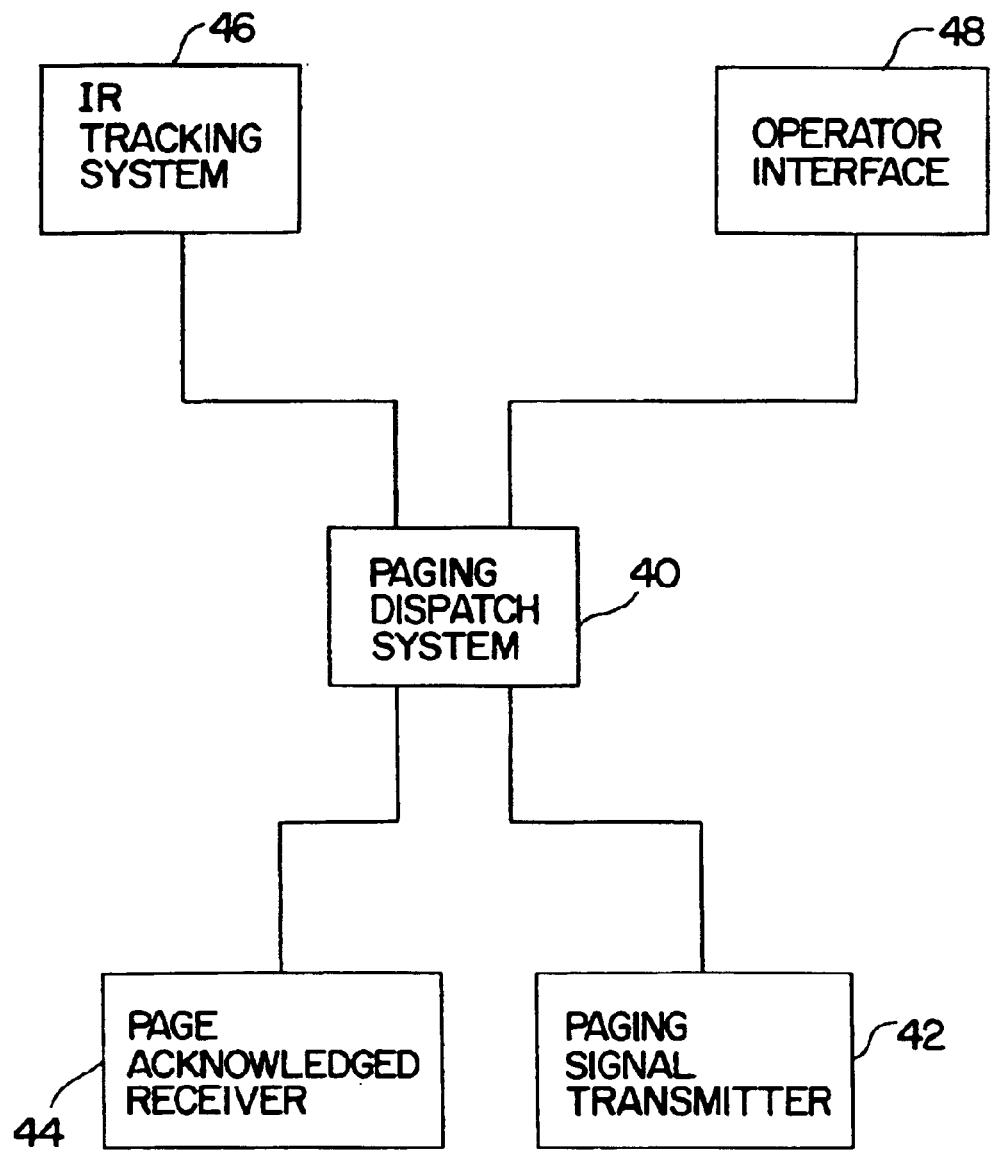
FIG. 10 is a block diagram showing an architecture of a paging system for use with the integrated device of FIG. 9.

Due to high costs associated with medical services provided by teams of caregivers, such as a surgical team, there are tremendous cost savings available by reducing the amount of time needed in assembling such teams. The present invention addresses this issue as shown in FIG. 10 by providing each team member with an integrated device 10 and by using a paging dispatch system 40. Cellular paging and telephony module 30 of each integrated device 10 assigned to a particular team can readily be configured to receive a predefined paging signal and alert the caregiver via an audible alert or vibration when the signal is received. Thus, when dispatch system 40 transmits the predefined paging signal, it will be received simultaneously by each team member. To facilitate utility, integrated device 10 provides for reprogramming the paging signal or signals to which a particular device will respond.

Paging signal dispatch system 40 includes a transmitter 42 for sending paging signals as well as a receiver 44 for receiving page acknowledge return signals from each of the plurality of integrated devices 10. Transmitter 42 can be configured to send as many different paging signals as there are teams defined. The paging signal can be a direct, short-range radio frequency signal if all devices 10 are relatively nearby, such as within a hospital complex, or it can be an indirect, or repeated signal generated by a repeater such as is used by conventional cellular or telephony based paging systems to reach personnel who may be on call at unknown locations, or it can be a combination of the two types of signals.

In order to expedite assembly of a medical team, an acknowledgment from each member that a paging signal has been received is used. Again, as with the paging signal itself, the acknowledge return signal can be implemented in a variety of ways, such as by a direct, short-range radio frequency signal within the same complex as dispatch system 40 using either radio or data communication module 32, 34, or the acknowledge return signal can come as a return telephone call over a cellular network using cellular paging and telephony module 30, etc.

Referring to FIG. 1, integrated device 10 provides "answer" button 18 that initiates a short-range radio frequency acknowledge signal and "call" button 16 that initiates a cellular telephone call. The acknowledge call can be to a number provided to integrated device 10 with data encoded by the paging signal. In any case, dispatch system 40 understands which responding device 10 is acknowledging its page. Dispatch system 40 is configured to determine which team members acknowledged the page and can signal an alert if one or more members fail to acknowledge within a predetermined amount of time of having sent the paging signal. This amount of time can vary from a matter of seconds, e.g., if the page is for a life threatening situation, to a matter of minutes or even hours, i.e., for non-emergency situations.

Referring back to FIG. 10, Infrared transmitter module 38 allows for integrated device 10 to be used with an infrared personnel tracking system 46. A coded IR signal unique to each integrated device 10 is received by IR receivers positioned throughout a facility in which tracking is desired, such as a hospital. IR tracking system 46, such as those described in application Ser. No. 08/963,396 entitled Personnel and Asset Tracking Method and Apparatus and in application Ser. No. 08/960,425 entitled Active Badge or Tag for a Locating and Tracking System, both of which are hereby incorporated by reference, is coupled to paging dispatch system 40 as shown in FIG. 10. Although an infrared-based tracking system using an infrared transmitter module 38 is shown, other personnel tracking technologies can be used, such as a tracking system based on RF transmitters, or ultrasound transmitters, etc.

When dispatch system 40 detects a failure to acknowledge a paging signal, it can provide the location of the non-acknowledging device 10 via an operator interface 48. Alternatively, a backup team member can be identified by tracking the locations of potential replacements and identifying one that meets specified criteria, such as proximity to the needed location or having a known availability status, etc. The paging dispatch system 40 can automatically page the replacement team member, or provide location information so that a critical team member can be tracked down manually, or provide location information on both the non-acknowledging team member and alternative replacements, etc. Operator interface 48 can be provided as a visual, e.g., textual and graphical interface, or it can be an electronic data interface to another system.

Integrated device 10 further enhances communication between members of a medical team by providing for two-way radio communication using module 32. Again, these RF technologies are well understood in the electronic arts. Integrated devices 10 allocated to different teams are configured to transmit on different predefined frequencies so that teams do not interfere with each other.

As mentioned above, integrated device 10 includes voice recording module 28. Once again, such technologies are well known to those in the art and can be implemented with a single integrated circuit, or can be included as a function of a digital signal processor that implements other functions of device 10, etc. In order to facilitate hands-free operation of device 10, voice recording module 28 can be configured to be voice-activated. Using techniques as are known in the art, voice recording module 28 can respond only to the appropriate voice print, or can be configured to require an identification number before providing voice recording features. Voice recording module 28 can store recorded information in memory provided by controller 26, or recorded data can be sent by data communication module 34 to a remote system (not shown).

By transmitting voice data in real-time to a remote system, integrated device 10 provides the ability to store essentially unlimited amounts of dictation. This allows the caregiver, such as a doctor or a nurse, to dictate reports on procedures, patient status, etc., during the course of his or her activities, alleviating the need to allocate post-activity time to dictating reports. This results in both time and cost efficiencies that benefit medical service providers as well as patients. It also tends to improve the quality of reports due to the ease of making them at the appropriate time while memory is still fresh.

Voice recording module 28 is further enhanced by data communication module 34 which allows patient information to be obtained from a remote hospital data system. Controller 26 and voice recording module 28 can be configured to use speech recognition to identify a patient's name or accept entry of some other indicia such as a patient identification number, and transmit this information to the remote data system using data communication module 34. The remote hospital data system then provides specific patient history to controller 26. User input/output module 36 includes a display, such as a backlit liquid crystal display, that provides this information to the medical caregiver. By interfacing with the hospital data system, device 10 can further be configured to prompt the caregiver to provide specific information, such as Joint Commission Required Vitals to ensure compliance with required procedures.

A video communication module 35 further enhances utility of integrated device 10 by providing for communication of video data. Some surgical procedures use miniaturized video cameras (not shown), such as in an endoscope, the signals from which can be transmitted over either a video cable or via wireless communication. Video communication module 35 provides for receiving video signals from a video medical device (or any other video source) and then transmitting the video data to another system, such as a hospital data system, which can retransmit the video data as desired. Video communication module 35 provides for coupling integrated device 10 to a display system such as a computer system with video hardware to view video of a medical procedure, video of a person with whom a caregiver is communicating using device 10, or video from any source.

Cellular paging and telephony module 30 further provides a standard cell telephone capability for integrated device 10. As with cell telephones, a speed dial capability can be provided to facilitate one button dialing of important numbers. As discussed above, a paging signal can encode a telephone number that integrated device 10 will display and dial when the caregiver presses button 16 as shown in FIG. 1.

In order to facilitate use of integrated device 10 in a medical environment, a flexible sterile sheath, such as thin latex rubber, is provided to allow its transportation into a sterile field of an operating room. In its wrist band configuration, housing 10 is sufficiently smooth and has a thin enough profile to fit beneath a surgical glove. In either case, use of thin rubber to provide a sterile sheath can still allow the caregiver to view the backlit liquid crystal display.

Figure 5:
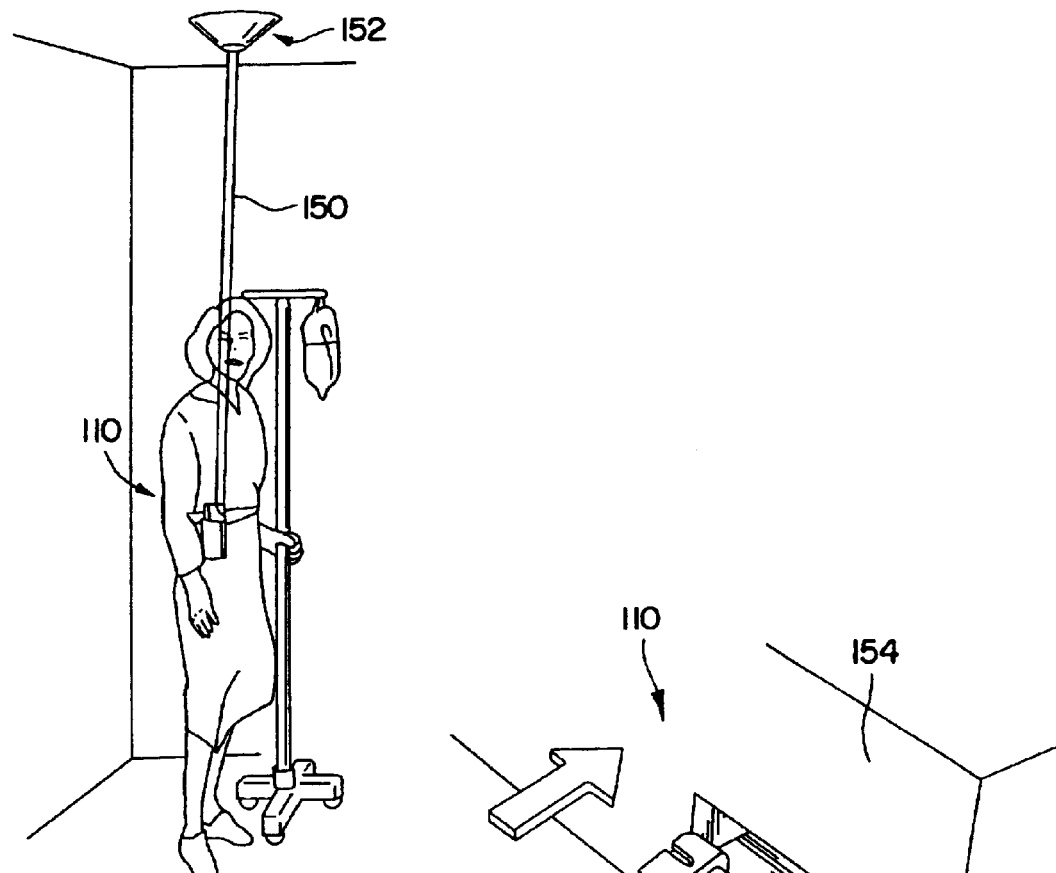
FIG. 5 is a perspective view of an alternative embodiment device according to the present invention coupled to a caregiver's belt and configured to send a signal to a ceiling-mounted receiver for tracking personnel location.
Figure 6:
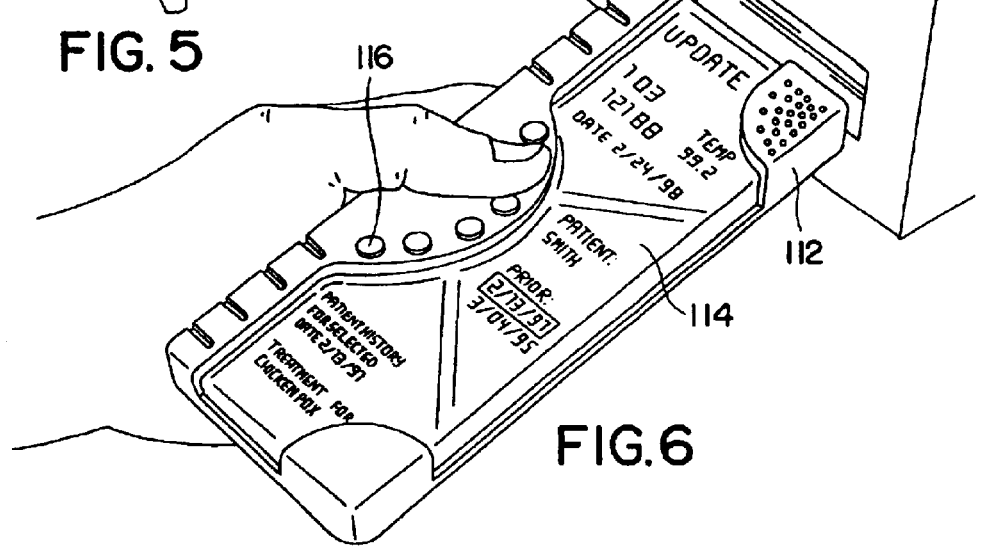
FIG. 6 is a perspective view of the device of FIG. 5 showing a display with patient information stored within the device, a microphone, user input buttons, and a data interface for uploading information.

An alternative embodiment integrated communication and data entry device 110, shown in FIGS. 5–6, is configured as a hand-held unit with a generally rectangular housing 112, relatively large, tri-segment backlit LCD display 114, and several buttons 116. Integrated device 110 includes an IR transmitter that sends a coded IR signal 150 for reception by an IR receiver 152 as shown in FIG. 5. Display 114 as shown in FIG. 6 illustrates exemplary patient data that can be downloaded from and uploaded to a remote system. Device 110 also includes a data interface connector (not shown, but any suitable type such as a PCMCIA interface) to allow for directly coupling to a remote hospital data system 154 for exchange of data.

Figure 7:
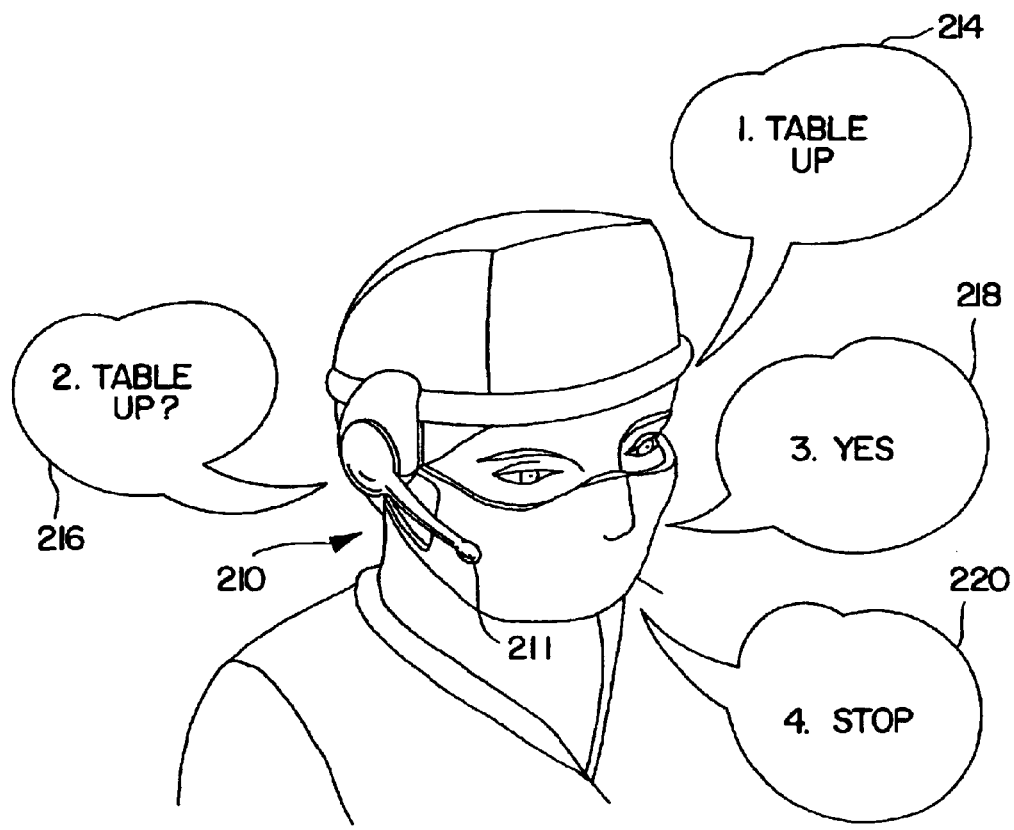
FIG. 7 is a perspective view of a medical caregiver wearing a head-mounted, voice-operated medical equipment controller.
Figure 8:
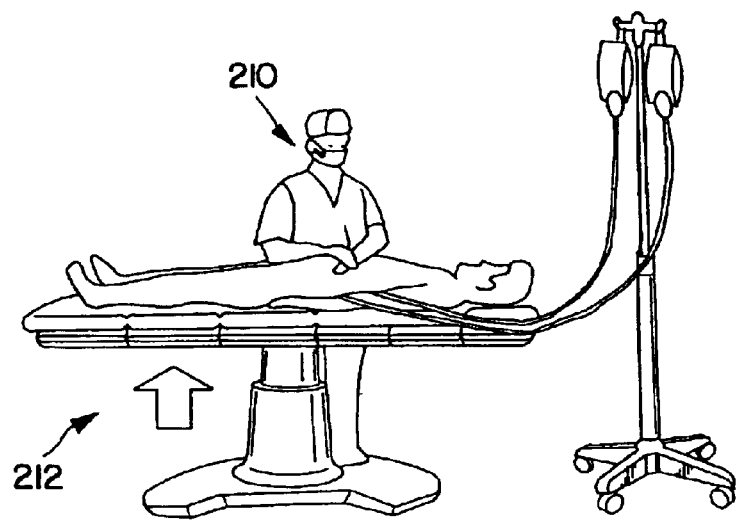
FIG. 8 is a perspective view showing the caregiver of FIG. 7 using the voice-operated controller to command a surgical table.

A head-mounted, voice-operated controller 210 for medical equipment is shown in FIGS. 7 and 8. Controller 210 is configured with a microphone 211 that extends towards the operator's mouth to minimize sensitivity to extraneous noise. By using speech recognition technology as is known in the art, controller 210 can take oral commands from a caregiver and transmit them over a wireless communication link to control medical equipment that is coupled to a receiver (not shown) configured to receive the commands. The speech recognition itself can be performed by the receiver, with controller 210 only transmitting digitized voice data. The voice command features of controller 210 can be incorporated into integrated device 10.

The voice commands can be interlocked as shown in FIG. 7. The caregiver issues a voice command to move a surgical table 212 vertically up with a "table up" oral command 214. The receiver (not shown) interprets command 214 and sends a "table up?" request to acknowledge 216 that controller 210 transforms into an oral confirmation request to the caregiver, who then confirms the command with a "yes" acknowledgment 218. When table 212 has reached a sufficient height the caregiver issues a "stop" command 220, which the receiver promptly acts upon without requesting confirmation to stop vertical movement of table 212.

Although the invention has been described in detail with reference to certain preferred embodiments, variations and modifications exist within the scope and spirit of the present invention as described and defined in the following claims.

What is claimed is:

1. An integrated device comprising:
   a portable housing;
   an internal controller coupled to the housing;
   a transmitter coupled to the controller, the transmitter configured by the controller to transmit an identifying signal, the identifying signal uniquely identifying the integrated device;

an input device coupled to the housing, an output device coupled to the housing, a transceiver coupled to the housing to send and receive information over a wireless communication link to a hospital data system, wherein the integrated device is configured to accept input information from the input device, to send an outgoing message related to the input information to the hospital data system, to receive an incoming message from the hospital data system, and to communicate output information related to the incoming message with the output device; and a voice recording device coupled to the controller.

2. The integrated device of claim 1, wherein the voice recording device provides the input device.

3. The integrated device of claim 1, wherein the voice recording device provides the controller.

4. The integrated device of claim 1, further comprising a cellular telephone transceiver coupled to the controller.

5. The integrated device of claim 1, further comprising a radio transceiver for two-way communication coupled to the controller.

6. The integrated device of claim 1, wherein the integrated device is configured to transmit the input information to the hospital data system to enable storage of voice information from the voice recording device on the hospital data system.

7. The integrated device of claim 1, wherein the pager is configured to couple to a caregiver's wrist.

8. The integrated device of claim 1, wherein the voice recording device is configured to digitize voice data and to transform the digitized voice data into computer readable text data.

9. The integrated device of claim 1, further comprising a clock coupled to the controller and wherein the voice recording device is configured to record a time and date from the clock corresponding to recorded voice data.

10. The integrated device of claim 1, further comprising an input device to enter a user identification code and wherein the voice recording device is configured to record voice data only after entry of a predefined user identification code.

11. The integrated device of claim 1, wherein the voice recording device is configured to record voice data only if the voice data corresponds to predefined voice print information.

12. The integrated device of claim 1, wherein the housing is configured to be coupled to a caregiver's wrist.

13. The integrated device of claim 1, wherein the housing is configured to couple to a belt around a caregiver's waist.

14. The integrated device of claim 1, wherein the housing is configured to couple to a strap around a caregiver's neck.

15. The integrated device of claim 1, further comprising a flexible sterile sheath configured to surround the housing.

16. An integrated personal communication and data entry device comprising:

a portable housing;

an internal controller coupled to the housing;

a paging device coupled to the controller;

a voice recording device coupled to the controller;

an input device coupled to the housing, an output device coupled to the housing, a transceiver coupled to the housing to send and receive information over a wireless communication link to a hospital data system, and wherein the integrated device is configured to accept patient identification information from the input device, to send the patient identification information to the hospital data system, to receive patient data from the hospital data system based on the patient identification information, and to display the patient data on the output device.

17. The integrated device of claim 16, wherein the voice recording device provides the input device.

18. The integrated device of claim 16, wherein the output device comprises a backlit liquid crystal display.

19. The integrated device of claim 16, wherein the integrated device is configured to provide at least one prompt on the output device for entry of patient status information based on patient data received from the hospital system.

20. An integrated device comprising:

a portable housing;

an internal controller coupled to the housing;

an infrared transmitter coupled to the controller, the infrared transmitter configured by the controller to transmit an identifying signal, the identifying signal uniquely identifying the integrated device;

an input device coupled to the housing, an output device coupled to the housing, a transceiver coupled to the housing to send and receive information over a wireless communication link to a hospital data system, wherein the integrated device is configured to accept patient identification information from the input device, to send the patient identification information to the hospital data system, to receive patient data from the hospital data system based on the patient identification information, and to communicate the patient data with the output device; and a cellular telephone transceiver coupled to the controller.

21. The integrated device of claim 20, further comprising a radio transceiver for two-way communication coupled to the controller.

22. The integrated device of claim 20, further comprising a paging device coupled to the controller.

23. The integrated device of claim 20, further comprising a voice recording device coupled to the controller.

24. An integrated device comprising:

a portable housing;

an internal controller coupled to the housing;

an infrared transmitter coupled to the controller, the infrared transmitter configured by the controller to transmit an identifying signal, the identifying signal uniquely identifying the integrated device;

an input device coupled to the housing, an output device coupled to the housing, a transceiver coupled to the housing to send and receive information over a wireless communication link to a hospital data system, wherein the integrated device is configured to accept patient identification information from the input device, to send the patient identification information to the hospital data system, to receive patient data from the hospital data system based on the patient identification information, and to communicate the patient data with the output device; and a radio transceiver for two-way communication coupled to the controller.

25. The integrated device of claim 24, further comprising a cellular telephone transceiver coupled to the controller.

26. The integrated device of claim 24, further comprising a paging device coupled to the controller.

27. The integrated device of claim 24, further comprising a voice recording device coupled to the controller.

28. An integrated device comprising:

a portable housing;

an internal controller coupled to the housing;

a paging device coupled to the controller;

an input device coupled to the housing, an output device coupled to the housing, a transceiver coupled to the housing to send and receive information over a wireless communication link to a hospital data system, wherein the integrated device is configured to accept patient identification information from the input device, to send the patient identification information to the hospital data system, to receive patient data from the hospital data system based on the patient identification information, and to communicate the patient data with the output device; and an infrared transmitter coupled to the controller, the infrared transmitter configured by the controller to transmit an identifying signal on, the identifying signal uniquely identifying the integrated device.

29. The integrated device of claim 28, further comprising a cellular telephone transceiver coupled to the controller.

30. The integrated device of claim 28, further comprising a radio transceiver for two-way communication coupled to the controller.

31. The integrated device of claim 28, further comprising a voice recording device coupled to the controller.

* * * * *